(12) United States Patent
Darley et al.

(10) Patent No.: US 8,755,910 B2
(45) Date of Patent: Jun. 17, 2014

(54) REFERENCE ELECTRODES FOR INNER EAR STIMULATION DEVICES

(75) Inventors: Derek I. Darley, Cromer Heights (AU); Alf Dal'Castel, Cherrybrook (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 12/816,385

(22) Filed: Jun. 15, 2010

(65) Prior Publication Data

US 2012/0078337 A1    Mar. 29, 2012

(30) Foreign Application Priority Data

Jun. 15, 2009 (AU) ................................. 2009902734

(51) Int. Cl.
*A61N 1/36* (2006.01)

(52) U.S. Cl.
USPC ........................................................ 607/136

(58) Field of Classification Search
CPC .......................... A61N 1/0541; A61N 1/36032
USPC ............................ 607/136, 57, 40, 116, 137
See application file for complete search history.

(56) References Cited

U.S. PATENT DOCUMENTS

| | | | | |
|---|---|---|---|---|
| 4,284,085 A * | 8/1981 | Hansen et al. | ............... | 607/137 |
| 4,419,995 A * | 12/1983 | Hochmair et al. | ............. | 607/57 |
| 4,809,712 A * | 3/1989 | Kuzma | .......................... | 607/116 |
| 5,545,219 A * | 8/1996 | Kuzma | .......................... | 623/10 |
| 5,749,912 A | 5/1998 | Zhang et al. | | |
| 5,833,714 A | 11/1998 | Loeb | | |
| 6,671,559 B2 | 12/2003 | Goldsmith et al. | | |
| 6,889,094 B1 * | 5/2005 | Kuzma et al. | ................. | 607/137 |
| 6,968,238 B1 * | 11/2005 | Kuzma | .......................... | 607/137 |
| 2003/0069613 A1 * | 4/2003 | Kuzma et al. | .................... | 607/40 |
| 2003/0125785 A1 * | 7/2003 | Kuzma et al. | ................. | 607/116 |
| 2007/0282395 A1 * | 12/2007 | Maltan et al. | ................... | 607/57 |
| 2010/0204768 A1 * | 8/2010 | Jolly et al. | .................... | 607/137 |

* cited by examiner

*Primary Examiner* — Carl H Layno
*Assistant Examiner* — Paula J Stice
(74) *Attorney, Agent, or Firm* — K&L Gates, LLP

(57) ABSTRACT

A reference electrode for an inner ear stimulation device is disclosed. The reference electrode is to be implanted and includes a protruding conductor portion and an insulated conducting portion connected to a lead for connection to the device. The protruding conductor portion is shaped so as to present a generally smooth surface without any substantial projections to impede removal in the event that the electrode is withdrawn in the direction of the lead. The smooth profile and lack of an undercut assist in preventing biofilm accumulation and growth. This reduces the risk of post-surgical complications such as infection.

25 Claims, 3 Drawing Sheets

REFERENCE ELECTRODES FOR INNER EAR STIMULATION DEVICES

CROSS-REFERENCE TO RELATED APPLICATIONS

This application claims the benefit of Australian Provisional Patent Application 2009902734, filed Jun. 15, 2007, which is hereby incorporated by reference herein.

BACKGROUND

1. Field of the Invention

The present invention relates generally to electrodes for use in electrically stimulating medical devices, and more particularly, to extra-cochlear electrodes for use in stimulating hearing prostheses.

2. Related Art

Stimulating hearing protheses such as cochlear implants, vestibular array stimulation devices and auditory brain implants (ABIs) have been widely employed to assist those with sensorineural hearing loss. For example, in a cochlear implant, auditory sensations arise when a flow of electrical current between electrodes stimulates auditory neural tissue in the cochlea. The use of one or more reference electrodes implanted external to the cochlea, known as extra-cochlear electrodes (ECEs) allows alternative stimulation modes to be employed. In one conventional form, the ECE extends on its own lead, and is implanted external to the cochlea between the temporalis muscle and skull or other suitable anatomical location.

Two main stimulation modes are commonly used for stimulation. In bipolar mode, the selected active electrode and reference electrode are both positioned within the cochlea, typically close together. The use of an ECE allows for monopolar stimulation, in which current flows between an electrode within the cochlea, and an ECE. Monopolar stimulation generally produces auditory percepts using much lower current levels than is possible with bipolar modes of stimulation.

Existing ECEs are formed as so-called hardball electrodes, in which the tip of the electrode is formed as a small platinum ball. These electrodes, however, are not readily removable in the event that explanation is required. In particular, when a device is implanted into a tissue (such as when a reference electrode of a cochlear implant, is implanted under the temporalis muscle) the body's immune response causes tissue to encapsulate the device resulting in the device being mechanically locked, or keyed, into place. When it comes time for the device to be explanted, this encapsulation must be overcome, for example broken, so that the device can be removed. For a reference electrode, the force required to extract the electrode should be less than strength of the lead and/or electrode, or the lead and/or electrode may break during removal.

SUMMARY

In broad form, the present invention provides a reference electrode for an inner ear stimulation device, shaped so as to facilitate removal from tissue in the event that explanation is required.

According to one aspect, the present invention provides a reference electrode for an inner ear stimulation device having an insulated conducting portion connected to or forming a lead for connection to the inner ear stimulation device, wherein the conductive portion of the reference electrode is shaped without any substantial projections to impede removal in the event that the electrode is withdrawn from the patient. The insulated conducting portion can be one of an extra-cochlear electrode, or other conductive device for stimulating a portion of the inner ear electrically, mechanically or otherwise. The conductive portion of the reference electrode may be generally smooth, and may have a length substantially longer than its width.

Accordingly, the electrode enables simpler explanation and surgery in general.

BRIEF DESCRIPTION OF THE DRAWINGS

Illustrative embodiments of the present invention are described herein with reference to the accompanying figures, in which.

DETAILED DESCRIPTION

Exemplary aspects and embodiments of the present invention are described with reference to a particular illustrative example, which is a device intended for use in an intra-cochlear stimulation system. It may be applied to other stimulating medical devices and, in particular, other stimulating hearing prostheses which stimulate functions of the inner ear, which includes a cochlear stimulation electrode array, such as a hybrid electrical and acoustic hearing prosthesis system and a vestibular stimulation array for stimulating elements of the vestibular system, such as the semi-circular canals. It may be applied to a system with implanted components which communicate with external components, or to a fully implanted system. It will be appreciated that the present implementations are described for illustrative purposes, and their features are not intended to limit the scope of the present invention. Many variations and additions are possible within the scope of the present invention.

Figure 1:
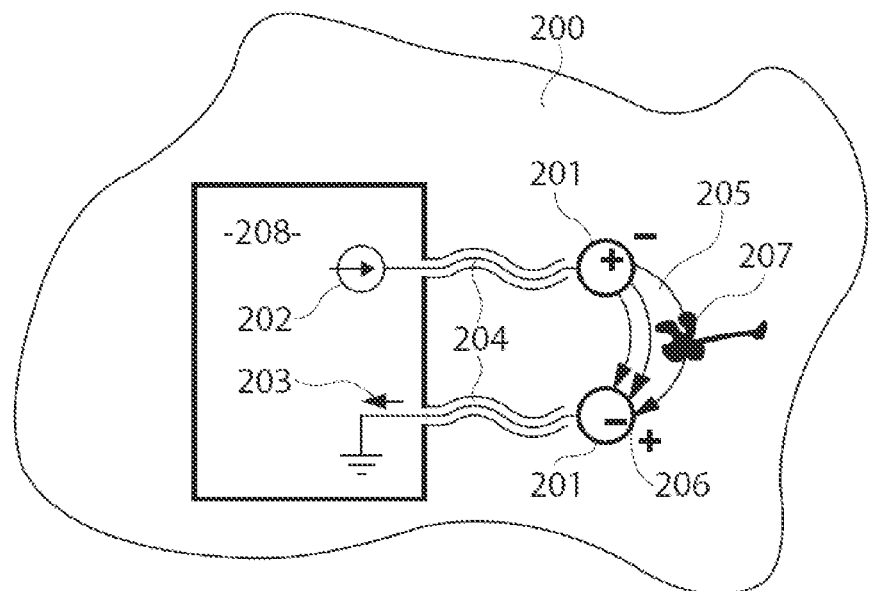
FIG. 1 is a general illustration of the principal of electrical auditory stimulation.

FIG. 1 is a schematic view illustrating the principle of electrical stimulation in a cochlear implant. Cochlear implants use direct electrical stimulation of auditory nerve cells to bypass absent or defective hair cells that normally transduce acoustic vibrations into neural activity. Such devices generally use electrodes inserted into the scala tympani of the cochlea so that the electrodes may differentially activate auditory neurons that normally encode differential pitches of sound. Similar devices such as the ABI are also used to treat a smaller number of patients with bilateral degeneration of the auditory nerve. For such patients, the ABI provides stimulation of the cochlear nucleus in the brainstem.

Exemplary prostheses in which the present invention may be implemented include, but are not limited to, systems presently sold by Cochlear Limited of Australia. As described therein, cochlear implants generally include an external, wearable control unit that determines a pattern of electrical stimulation that is provided to an implanted stimulator unit containing active circuitry in a hermetic enclosure. Electrical stimuli are delivered through electrodes to provide electrical stimulation of auditory nerve cells.

In general terms, implanted electrodes are selectively driven with a current in order to evoke a perception of sound for the user. FIG. 1 illustrates this schematically. The platinum electrodes 201 are connected to an implant 208 via insulated wires 204 and driven by the stimulating current 202, which passes through the tissue 200 and the nerve cell 207, and returns to the implant 208 (return current 203). At the surface of the platinum electrodes 201, chemical reactions take place, changing the electron current in the electronics to an ion current 205 in the tissue; charge 206 remains on the electrode surface, causing an increase in voltage across the interface.

Figure 2:
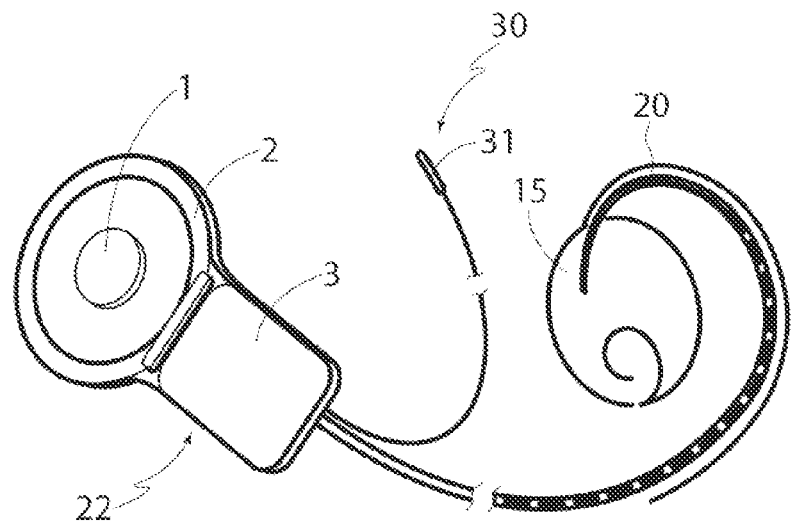
FIG. 2 illustrates one implementation of the present invention.

FIG. 2 illustrates an implementation of the present invention. Receiver stimulator unit 22 includes an implantable coil 2 for communicating with external devices, as well as a magnet 1 to assist in aligning the implantable coil with a corresponding external coil. Receiver stimulator unit 22 includes sealed unit 3, containing a processor (not shown) for generating stimuli. From sealed unit 3 extends the intra-cochlear electrode array 20, located in the scala tympani 15, and the extra-cochlear electrode 30. Extra-cochlear electrode 30 terminates in protruding conductor portion 31.

Figure 3:
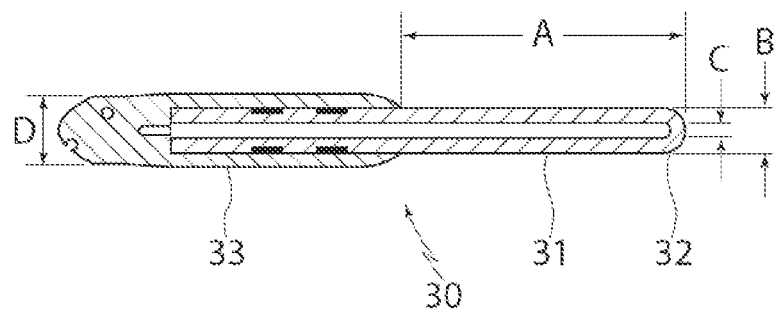
FIG. 3 illustrates the electrode tip region of FIG. 2 in more detail.

FIG. 3 illustrates one implementation of the electrode in more detail. The extra-cochlear reference electrode 30 is formed from an exposed streamlined protruding conductor portion 31, in the form of a tube, having an exposed length A, external diameter B and internal diameter C (preferably, A is 4.0 mm, B is 0.6 mm and C is 0.2 mm) with a hermetic dome-shaped end 32 composed of a biocompatible and electrically conductive material, for example platinum. The electrode tube 31 extends into a silicone moulding 33, which provides an insulated conducting portion of the electrode 30, having a diameter D, which is preferably 0.9 mm, which also encloses the electrical connection, or lead, to the stimulator. However, an alternative embodiment may be that the silicon moulding 33 only insulates the lead and, therefore, the lead itself is the insulated conducting portion, with the protruding conducting portion consisting of electrode only. It will be appreciated that any suitable biocompatible insulator could be used in place of the silicone and that the measurements provided above are merely illustrative and could be modified by one skilled in the art based on the application and desired characteristics of the device. Similarly, it will be appreciated that the tube could be formed from any suitable alternative biocompatible conductor, for example, platinum iridium alloy, or titanium.

The shape of the illustrative electrode, having a streamlined tube 31 and a dome shaped tip 32, eases surgery, particularly explanation. It will be appreciated that there are many possible shapes for the electrode according to the present invention. The smooth surface of the tube, without shoulder or other protrusions, and hemispherical profile of the tip, do not allow tissue or bone ingrowth to retain the electrode or tip, thereby simplifying surgical explanation. In particular, the transition region of the tube 31 and tip 32 has a transition angle of 0 degrees. That is, the protruding conductor portion does not vary in width from the tube 31 to the tip 32.

A transition region, in the context of this description, is the region between a proximal end portion and a distal end portion of the protruding conductor portion (as compared to the insulated conducting portion), which may be of greater, lesser or the same width. A transition region having a transition angle of 0 degrees implies no change in width between the proximal end portion and the distal end portion.

A shoulder, in the context of this description, is a transition region, having a transition angle greater than 45 degrees, where the transition angle is measured from an extension of a datum parallel to the surface of the proximal end portion and the surface of the distal end portion where it is attached to the proximal end portion. For further clarification, an example of this measurement is shown as angle 66 in FIG. 6. If the transition angle was greater than 90 degrees, this would mean that the distal end portion shape begins by going back upon the proximal end portion. A negative angle means that the distal end portion narrows when compared with the proximal end portion.

In this manner, tissue damage and/or disruption is minimised using the electrode of FIG. 3 during surgical explanation. This presents highly favourable benefits for surgeons and patients alike, including ease of surgical explanation, and reduced operation time. Further, the smooth profile may assist in minimizing any impact from biofilm accumulation and growth. This reduces the risk of post-surgical complications such as infection.

It will be appreciated that different shapes are possible which, none the less, are functional to achieve the desired outcome. The design is preferably generally smooth with no sharp edges. By generally smooth it is intended to encompass tapered and constant cross sections, as well as smoothly varying cross sections and shapes. The shape may have intermediate regions which are of greater diameter than the tip or the region adjacent the insulated conducting portion. By substantial projections it is meant abrupt discontinuities in the surface, barbs, shoulders, ribs, and so forth which would impede removal in the event that explanation is required.

For example, one prior art reference electrode comprises a protruding conductor portion having an proximal end portion terminating in an distal end portion comprising three circular discs in a clover arrangement. As such, there is a shoulder region between the proximal end portion and the distal end portion where the conducting portion splays out abruptly and transitions for only a short distance. The angle of the transition region is approximately 60 degrees. The width, or largest cross-sectional diameter, of the distal end portion is approximately 300% the width of the proximal end portion and the length is, approximately, less than three times the width of the proximal end portion, so that the distal end portion is bulbous on the proximal end portion. The shoulder region, as described above, of this type of electrode may cause the electrode to become mechanically locked.

Other prior art reference electrodes, such as the hard-ball electrode mentioned previously, comprise of a similar proximal end portion with a spherical "ball" electrode as the distal end portion. The shoulder for this type of electrode has an angle at the transition region between the proximal end portion and the ball of approximately 90 degrees. Again the width of the ball electrode is around 300% of the lead body, but may be less, and less than three times the width of the lead. The shoulder region causes the electrode to become mechanically locked and can cause the proximal end portion of the electrode or the lead to break during explanation, leaving the ball electrode embedded in the patient, which is particularly difficult to retrieve.

Generally, an increase in the width towards the distal end of a reference electrode will result in keying or mechanically locking the device within the body. To avoid mechanically locking the device when there is an increase of width greater than 50% of the width of the proximal end portion, the transition region from the proximal end portion to the distal end portion should have a transition angle of less than 45 degrees. More preferably the angle is less than 30 degrees and, even more preferably less than 10 degrees.

In the case of an increase of width of less than 50% of the width of the proximal end portion, a transition angle of 90 degrees or less may be acceptable.

Whatever the increase in width, it is preferable to have smooth transitions between surfaces by incorporating, for example, a fillet or concave easing of an interior corner and a round or convex easing of an external corner. So, if a transition angle of 90 degrees is used, because the increase in width of the distal end portion is less than 50%, it is preferable to use a fillet at the 90 degree corner to decrease any amount of mechanical locking that does occur.

It is preferable that there is less than 10% increase in width along the length of the protruding conducting portion with respect to the proximal end and, preferably substantially 0% increase in width.

Figure 4:
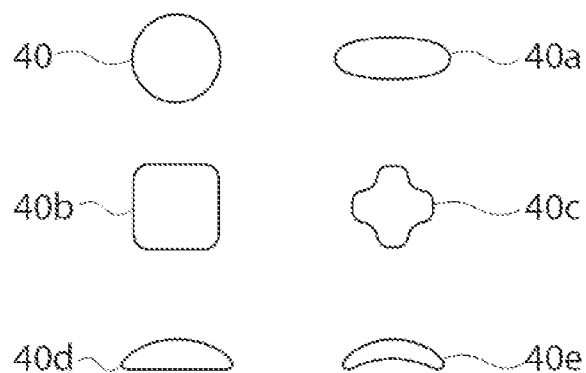
FIG. 4 illustrates examples of alternative cross-sectional shapes for the electrode.

FIG. 4 illustrates alternative cross sectional shapes 40, 40a, 40b, 40c, 40d and 40e for the extra-cochlear electrode array. The shapes can generally be described as follows: circular 40, oval 40a, square with rounded corners 40c, cross with rounded corners 40b, convex upper surface and flat lower surface with rounded transition between surfaces 40d and convex upper surface and concave lower surface with rounded transition between surfaces 40e. The invention may be implemented with any suitable cross sectional shape which does not have sharp edges or micro gaps. Certain cross-sectional shapes can increase the surface area of the protruding conductor portion of the electrode and, therefore, may be more desirable. Simplicity of manufacture also influences cross-sectional shape choice.

Figure 6:
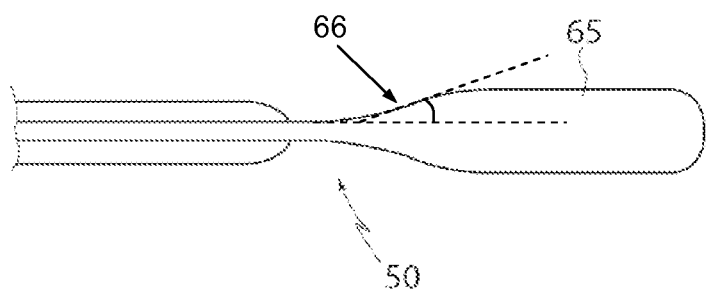
FIG. 6 illustrates a further alternative implementation of the electrode.

The cross section can change over the length, either increasing or decreasing, as long as the taper is smooth without creating sharp edges or shoulders. FIG. 6 illustrates conceptually an electrode 50 with a distal end portion 65 exhibiting a change in cross sectional width, without a shoulder. That is, the transition region between the proximal end portion of the electrode and the distal end portion 65 has a transition angle 66 of around 20 degrees. The width of the distal end portion 65 is around three times the width of the proximal end portion, thereby providing sufficient surface area to correctly operate as a reference electrode in this example.

Figure 7:
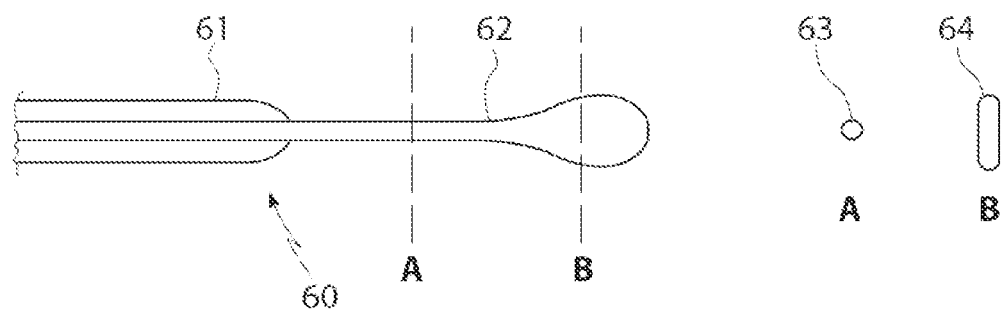
FIG. 7 illustrates another alternative implementation of the electrode.

Alternatively, the cross section could change to have a differently shaped profile along its length. In FIG. 7, for example, the electrode 60 has a conducting portion 62, having a first cross section shape (circular) 63 at point A, on the proximal end portion, close to the insulated conductor portion 61, and a second shape (oblong with hemispherical ends) 64 at B, further from the insulated conductor portion at the distal end portion, with a smooth transition region between them. Again, the transition angle is approximately 20 degrees.

It will be appreciated that because of the function of the reference electrode, and the issues of charge transfer, there are minimum requirements for the exposed surface area of the electrode. These parameters may vary between different stimulation devices, and any practical implementation will need to take account of the intended stimulation system. For the Nucleus system, available commercially from Cochlear Limited, an exposed area of 6.3 mm$^2$ has been proven to be adequate. Smaller sizes may result in unintentional percepts and unintended stimulation of the muscles, but size variations—both larger and smaller—may be acceptable based on the physical characteristics of the device and stimulation characteristics. Increasing the surface area may have improved effects such as decreased impedance and charge density. Implementations of the present invention allow for increasing the surface area without negatively impacting the performance and surgical useability.

Figure 5:
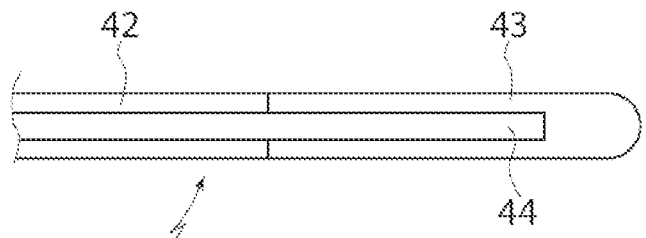
FIG. 5 illustrates an alternative implementation of the electrode.

FIG. 5 illustrates another alternative electrode, in which the extra-cochlear reference electrode 41 has a conducting portion 43, 44 which is flush to the silicone carrier 42. For example, the electrode may be 0.9 mm in diameter, thus it could be shorter and maintain the required surface area. This implementation is shown as fabricated from two tubes 44, 43 overlaid to provide the required thickness. In this case, the conducting portion 43 has an proximal end portion which extends from the silicone carrier 42 to a hemispherical end (as described in relation to FIG. 3), the hemispherical end being equivalent to the distal end portion and, therefore, the transition region having an angle of 0 degrees.

It will be appreciated that it is desirable that the protruding conductor is generally elongate, so that it is longer than the widest part of the protruding conductor, or alternatively longer than the average width of the protruding conductor. This allows for the required surface area to be provided by having a longer electrode, and hence of generally narrower diameter, than prior art ball type electrodes.

As mentioned above, and for the avoidance of doubt, the insulated conducting portion can comprise, either singly or combined, a lead (connected to a stimulator) and a portion of an electrode with any portion which is protruding from the insulated conducting portion being the protruding conducting portion.

There will now be described a preferred manufacturing technique for the extra-cochlear reference electrode tip implementation described with reference to FIG. 3.

The process begins with a platinum tube, preferably 99.95% pure. The tube should have an outer diameter of 0.6 mm, and an inner diameter of 0.2 mm.

This tube undergoes EDM (Electrical Discharge Machining) cutting to create a uniform end with minimal burr. With the EDM cutting process to prepare the surface for the formation of the dome, the process is highly automated resulting in greater accuracy and has demonstrated minimal burring.

The cut to length tubes are then held in a tooling plate (fixture) for loading onto a CNC (Computed Numerically Controlled) x-y positioning system allowing for automation of the dome-shaping process. An automated laser spot welding process is employed to form the hermetic dome. The uniform dome is produced on the end of a platinum tube via a pulsed laser. The pulsed laser is preferably of a type that utilises hard-optic or fibre optic beam-delivery, for example includes a laser Nd:Yag (neodymium: yttrium aluminium garnet).

The laser fires a single beam at the tube generating sufficient heat to melt the end. Due to surface tension, the molten metal forms the dome-shaped end upon solidification. This process rapidly generates uniform domes of dimensional and geometrical consistency. As this process is highly automated, uniform hermetic domes with no voids, a smooth surface, and a specified wall thickness, can be consistently formed. It will be appreciated that alternative manufacturing processes may be used to form the tip, for example an oxy-acetylene flame, or by electric spark generation.

After the extra-cochlear reference electrode tip is manufactured it is attached (crimped or laser welded) to a helix shaped platinum/iridium lead, and overmoulded in silicone, leaving the distal 4 mm exposed. The proximal end of the lead is attached to the stimulator.

It will be appreciated that the present invention may be implemented in many different forms, and in many different systems, and that such modifications and additions are encompassed within the scope of this disclosure.

What is claimed is:

1. A reference electrode for an inner ear stimulation device, the electrode including:
   a protruding uninsulated first conductor portion; and
   an insulated second conducting portion connected to or forming a lead for connection of the protruding uninsulated first conductor portion to the inner ear stimulation device;
   wherein the protruding uninsulated first conductor portion is shaped so as to present a generally smooth surface without any substantial projections to impede removal in the event that the electrode is withdrawn in the direction of the lead;
   wherein the protruding uninsulated first conductor portion has a proximal end portion and a distal end portion; and
   wherein the distal end portion has a width less than 10% of the width of the proximal end portion, the width of the distal end being no less than substantially equal to the width of the proximal end.

2. A reference electrode according to claim 1, wherein the tip of the protruding uninsulated first conductor portion has a hemispherical shape.

3. A reference electrode according to claim 1, wherein the cross sectional shape of the conductor portion is selected from one of the following: circular, oval, square with rounded corners, cross with rounded corners, convex upper surface and flat lower surface with rounded transition between surfaces and convex upper surface and concave lower surface with rounded transition between surfaces.

4. A reference electrode according to claim 1, wherein the protruding conductor has a shape which is generally smooth and elongate, so that the length of the protruding conductor is substantially larger than the width of the protruding conductor.

5. A reference electrode according to claim 1, wherein the reference electrode is an extra-cochlear electrode.

6. A reference electrode for an inner ear stimulation device, the electrode including:
   a protruding uninsulated first conductor portion; and
   an insulated second conducting portion connected to or forming a lead for connection of the protruding insulated conductor portion to the inner ear stimulation device;
   wherein the protruding uninsulated first conductor portion is shaped so as to present a generally smooth surface without any substantial projections to impede removal in the event that the electrode is withdrawn in the direction of the lead;
   wherein the protruding uninsulated first conductor portion has a proximal end portion and a distal end portion with a transition region therebetween;
   wherein the distal end portion has a width greater than 50% of the width of the proximal end portion; and
   the transition region has a transition angle, relative to the distal end portion, of less than 45 degrees.

7. A reference electrode according to claim 6, wherein the transition angle is less than 30 degrees.

8. A reference electrode according to claim 6, wherein any internal corner between the transition region and the proximal or distal end portion comprises a fillet.

9. A reference electrode according to claim 6, wherein any external corner between the transition region and the proximal or distal end portion comprises a round.

10. A reference electrode according to claim 6, wherein the transition angle is defined as an angle between a long axis of the protruding portion and a line substantially tangent to a surface of the distal end portion, the line substantially intersecting a point at which the distal end portion joins the proximal end portion.

11. A reference electrode according to claim 6, wherein the cross sectional shape of the conductor portion is selected from one of the following: circular, oval, square with rounded corners, cross with rounded corners, convex upper surface and flat lower surface with rounded transition between surfaces and convex upper surface and concave lower surface with rounded transition between surfaces.

12. A reference electrode according to claim 6, wherein the protruding conductor has a shape which is generally smooth and elongate, so that the length of the protruding conductor is substantially larger than the width of the protruding conductor.

13. A reference electrode according to claim 6, wherein the reference electrode is an extra-cochlear electrode.

14. A reference electrode for an inner ear stimulation device, the electrode including:
    a protruding uninsulated first conductor portion; and
    an insulated second conducting portion connected to or forming a lead for connection of the protruding insulated conductor portion to the inner ear stimulation device;
    wherein the protruding uninsulated first conductor portion is shaped so as to present a generally smooth surface without any substantial projections to impede removal in the event that the electrode is withdrawn in the direction of the lead;
    wherein the protruding uninsulated first conductor portion has a proximal end portion and a distal end portion with a transition region therebetween; and
    wherein the distal end portion has a width less than 50% of the width of the proximal end portion, the width of the distal end being no less than substantially equal to the width of the proximal end.

15. A reference electrode according to claim 14, wherein the transition region has a transition angle of less than 90 degrees.

16. A reference electrode according to claim 15, wherein the transition angle is defined as an angle between a long axis of the protruding portion and a line substantially tangent to a surface of the distal end portion, the line substantially intersecting a point at which the distal end portion joins the proximal end portion.

17. A reference electrode according to claim 14, wherein any internal corner between the transition region and the proximal or distal end portion comprises a fillet.

18. A reference electrode according to claim 14, wherein any external corner between the transition region and the proximal or distal end portion comprises a round.

19. A reference electrode according to claim 14, wherein the width of the distal end portion is substantially the same as the width of the proximal end portion of the protruding uninsulated first conductor portion.

20. A reference electrode according to claim 19, wherein the protruding uninsulated first conductor portion includes:
    an inner conducting part extending into the insulated second conducting portion; and
    an outer conducting part disposed on the inner conducting portion in a cap-like arrangement.

21. A reference electrode according to claim 20, wherein:
    a width of the outer conducting part is substantially the same as the width of the insulated second conducting portion.

22. A reference electrode according to claim 1, wherein the protruding uninsulated first conductor portion has a cross sectional shape substantially identical to the insulated second conducting portion at the point at which the portions meet.

23. A reference electrode according to claim 14, wherein the cross sectional shape of the conductor portion is selected from one of the following: circular, oval, square with rounded corners, cross with rounded corners, convex upper surface and flat lower surface with rounded transition between surfaces and convex upper surface and concave lower surface with rounded transition between surfaces.

24. A reference electrode according to claim 14, wherein the protruding conductor has a shape which is generally smooth and elongate, so that the length of the protruding conductor is substantially larger than the width of the protruding conductor.

25. A reference electrode according to claim 14, wherein the reference electrode is an extra-cochlear electrode.

* * * * *